(12) United States Patent
Costello et al.

(10) Patent No.: US 9,993,231 B2
(45) Date of Patent: Jun. 12, 2018

(54) DEVICES, SYSTEMS, AND METHODS FOR NAVIGATING A BIOPSY TOOL TO A TARGET LOCATION AND OBTAINING A TISSUE SAMPLE USING THE SAME

(71) Applicant: COVIDIEN LP, Mansfield, MA (US)

(72) Inventors: David M. Costello, Delano, MN (US); Thomas P. Crowley, Lino Lakes, MN (US); Thomas D. Magnuson, Plymouth, MN (US)

(73) Assignee: COVIDIEN LP, Mansfield, MA (US)

( * ) Notice: Subject to any disclaimer, the term of this patent is extended or adjusted under 35 U.S.C. 154(b) by 775 days.

(21) Appl. No.: 14/488,611

(22) Filed: Sep. 17, 2014

(65) Prior Publication Data

US 2015/0141869 A1 May 21, 2015

Related U.S. Application Data (60) Provisional application No. 61/906,771, filed on Nov. 20, 2013.

(51) Int. Cl.
*A61B 10/00* (2006.01)
*A61B 10/02* (2006.01)
*A61B 10/04* (2006.01)
*A61B 34/20* (2016.01)

(52) U.S. Cl.
CPC .......... *A61B 10/0266* (2013.01); *A61B 10/04* (2013.01); *A61B 2010/0208* (2013.01); *A61B 2034/2051* (2016.02)

(58) Field of Classification Search
CPC .... A61B 17/320758; A61B 2018/1861; A61B 10/0266; A61B 1/2676
USPC .............. 600/562, 564, 565, 566, 567, 568; 606/167
See application file for complete search history.

(56) References Cited

U.S. PATENT DOCUMENTS 3,732,858 A * 5/1973 Banko ................ A61B 10/0266
600/566
3,844,272 A 10/1974 Banko
3,882,849 A 5/1975 Jamshidi
(Continued)

FOREIGN PATENT DOCUMENTS

EP 2018112 A2 1/2009
WO 2007109418 A2 9/2007
(Continued)

OTHER PUBLICATIONS

International Search Report from corresponding PCT/US2014/058442 dated Dec. 26, 2014.
(Continued)

*Primary Examiner* — May Abouelela (57) ABSTRACT

A biopsy tool includes an elongated flexible body, a sensor assembly, and a screw member. The sensor assembly is disposed within the elongated flexible body towards the distal end thereof. The sensor assembly includes a location sensor(s) configured to enable detection of a location of the sensor assembly. The screw member is coupled to the distal end of elongated flexible body, extends distally from the elongated flexible body, and is positioned distally of the sensor assembly. The screw member defines a helical configuration having a hollow interior and is configured for simultaneous rotation relative to tissue and advancement into tissue to obtain a tissue sample.

19 Claims, 8 Drawing Sheets

(56) References Cited

U.S. PATENT DOCUMENTS

| | | |
|---|---|---|
| 4,111,207 A | 9/1978 | Seiler, Jr. |
| 4,177,797 A | 12/1979 | Baylis et al. |
| 4,662,869 A | 5/1987 | Wright |
| 4,682,606 A * | 7/1987 | DeCaprio ............ A61B 10/0266 |
| | | 600/567 |
| 4,702,260 A | 10/1987 | Wang |
| 4,708,147 A | 11/1987 | Haaga |
| 4,745,919 A * | 5/1988 | Bundy ............... A61B 17/3207 |
| | | 600/564 |
| 4,935,025 A * | 6/1990 | Bundy .................. A61B 10/04 |
| | | 600/564 |
| 5,018,530 A * | 5/1991 | Rank ................. A61B 17/3403 |
| | | 600/435 |
| 5,211,651 A * | 5/1993 | Reger ............. A61B 17/32075 |
| | | 606/159 |
| 5,226,909 A * | 7/1993 | Evans ............. A61B 17/32078 |
| | | 604/22 |
| 5,251,641 A | 10/1993 | Xavier |
| 5,437,266 A * | 8/1995 | McPherson ........ A61B 17/0218 |
| | | 600/217 |
| 5,615,690 A | 4/1997 | Giurtino et al. |
| 5,807,282 A | 9/1998 | Fowler |
| 6,083,237 A * | 7/2000 | Huitema ............ A61B 10/0233 |
| | | 600/567 |
| 6,162,214 A | 12/2000 | Mueller et al. |
| 6,302,903 B1 * | 10/2001 | Mulier ............... A61B 18/1477 |
| | | 606/41 |
| 6,371,928 B1 * | 4/2002 | Mcfann ................ A61B 17/221 |
| | | 600/434 |
| 6,451,036 B1 * | 9/2002 | Heitzmann ...... A61B 17/32075 |
| | | 606/159 |
| 6,709,408 B2 | 3/2004 | Fisher |
| 6,743,245 B2 | 6/2004 | Lobdell |
| 6,773,443 B2 | 8/2004 | Truwit et al. |
| 6,872,185 B2 | 3/2005 | Fisher |
| 6,890,309 B2 | 5/2005 | Fisher |
| 6,908,440 B2 | 6/2005 | Fisher |
| 6,981,949 B2 | 1/2006 | Hibner et al. |
| 7,189,206 B2 | 3/2007 | Quick et al. |
| 7,555,330 B2 | 6/2009 | Gilboa et al. |
| 7,969,143 B2 | 6/2011 | Gilboa |
| 7,998,062 B2 | 8/2011 | Gilboa |
| 8,241,225 B2 | 8/2012 | Seiger et al. |
| 8,262,585 B2 | 9/2012 | Thompson et al. |
| 8,343,072 B2 | 1/2013 | Bacon et al. |
| 8,343,073 B2 | 1/2013 | Miller |
| 8,506,503 B2 | 8/2013 | Fritscher-Ravens et al. |
| 8,532,748 B2 | 9/2013 | Leimbach et al. |
| 8,568,334 B2 | 10/2013 | Field et al. |
| 8,611,984 B2 | 12/2013 | Greenburg et al. |
| 8,641,640 B2 | 2/2014 | Lubock et al. |
| 8,784,333 B2 | 7/2014 | Corvi et al. |
| 8,821,411 B2 | 9/2014 | Berberich |
| 8,858,461 B2 | 10/2014 | Persat |
| 9,155,527 B2 * | 10/2015 | Vetter ................ A61B 10/0266 |
| 9,463,001 B2 * | 10/2016 | Vetter ................ A61B 10/0266 |
| 2002/0143270 A1 | 10/2002 | Miller |
| 2003/0114773 A1 * | 6/2003 | Janssens ............ A61B 10/0233 |
| | | 600/564 |
| 2009/0018468 A1 | 1/2009 | Janssens |
| 2009/0284255 A1 | 11/2009 | Zur |
| 2010/0016757 A1 | 1/2010 | Greenburg et al. |
| 2010/0241028 A1 | 9/2010 | Johnson et al. |
| 2013/0096459 A1 * | 4/2013 | Vetter .................... A61B 10/06 |
| | | 600/567 |
| 2013/0223702 A1 | 8/2013 | Holsing et al. |
| 2013/0331733 A1 | 12/2013 | Plishka et al. |
| 2014/0128770 A1 * | 5/2014 | Vetter .................... A61B 10/06 |
| | | 600/566 |
| 2014/0358029 A1 * | 12/2014 | Vetter ................ A61B 10/0266 |
| | | 600/567 |

FOREIGN PATENT DOCUMENTS

| | | |
|---|---|---|
| WO | 2011004776 A1 | 1/2011 |
| WO | 2012068315 A1 | 5/2012 |

OTHER PUBLICATIONS

European Search Report dated Jun. 23, 2017, issued in EP Application No. 14863619.

Japanese Office Action dated Aug. 17, 2018, in Japanese Appln. No. 2016531979.

* cited by examiner

DEVICES, SYSTEMS, AND METHODS FOR NAVIGATING A BIOPSY TOOL TO A TARGET LOCATION AND OBTAINING A TISSUE SAMPLE USING THE SAME

CROSS-REFERENCE TO RELATED APPLICATIONS

This application claims the benefit of, and priority to, U.S. Provisional Patent Appln. No. 61/906,771, filed on Nov. 20, 2013, the entire contents of which are incorporated herein by reference.

BACKGROUND

Technical Field

The present disclosure relates to biopsy sampling and, more particularly, to devices, systems, and methods for navigating a biopsy tool to a target location and obtaining a tissue sample using the biopsy tool.

Description of Related Art

A bronchoscope is inserted into a patient's airways through the patient's nose or mouth. A typical bronchoscope includes an elongated flexible tube having an illumination assembly for illuminating the region distal to the bronchoscope's tip, an imaging assembly for providing a video image from the bronchoscope's tip, and a working channel through which instruments, e.g., diagnostic instruments such as biopsy tools and/or therapeutic instruments such as ablation probes, can be inserted.

Bronchoscopes are limited in how far they may be advanced through the airways due to their size. Where the bronchoscope is too large to reach a target location deep in the lungs, a locatable guide ("LG") enveloped by a sheath is often utilized to navigate from the end of the bronchoscope to the target location. That is, the LG, together with a navigation system, enables the position and orientation of the LG to be tracked as the LG is advanced through the airways.

In use, the LG/sheath combination is inserted through the working channel of the bronchoscope and into the patient's airways. Once the LG has been navigated to the target location, aided by the position and orientation tracking provided by the navigation system, the LG is retracted through the sheath, leaving the sheath in position. With the LG retracted, the sheath is often referred to as an extended working channel ("EWC") because it effectively functions as an extension of the working channel of the bronchoscope.

Once the LG has been retracted from the EWC, the EWC may be used as an avenue for guiding working tools, e.g., biopsy tools, ablation probes, etc., to the target location. However, once the LG is removed from the EWC, tracking is no longer provided and, thus, the operator is operating blind, relying on the EWC to remain fixed at the target location. Repositioning of the working tool at the target location is likewise required to be performed without guidance.

SUMMARY

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

Provided in accordance with the present disclosure is a biopsy tool including an elongated flexible body, a sensory assembly, and a screw member. The sensor assembly is disposed within the elongated flexible body towards the distal end of the elongated flexible body. The sensor assembly includes at least one location sensor configured to enable detection of a location of the sensor assembly within a patient's airways. The screw member is coupled to the distal end of the elongated flexible body, extends distally from the elongated flexible body, and is positioned distally of the sensor assembly. The screw member defines a helical configuration having a hollow interior and is configured for simultaneous rotation relative to tissue and advancement into tissue to obtain a tissue sample within the hollow interior.

In aspects, the biopsy tool further includes a proximal handle portion coupled to a proximal end of the elongated flexible body. The proximal handle portion includes a housing having a drive motor disposed within the housing. The drive motor is configured to rotate the screw member.

In aspects, the proximal handle portion further includes an actuator configured for selectively activating the drive motor. The proximal handle portion may further include a battery disposed within the housing and configured such that actuation of the actuator completes an electrical circuit between the battery and the drive motor to activate the drive motor.

In aspects, the proximal handle portion is configured for manual manipulation to drive rotation of the screw member.

In aspects, the screw member is rigid, e.g., made of stainless steel.

In aspects, the screw member defines a distal cutting tip. The screw member may additionally or alternatively include one or more proximally-facing barbs.

In aspects, the screw member includes first and second screw arms. Each screw arm defines a helical configuration.

In aspects, the screw member includes a support plate secured to the exterior of the screw member and extending longitudinally along the screw member. The support plate is configured to maintain a fixed axial length of the screw member.

In aspects, the support plate defines sharpened longitudinal edges to facilitate cutting tissue.

In aspects, the support plate is affixed to at least two different turns of the screw member.

In aspects, the sensor assembly includes a sensor housing enclosing the at least one location sensor therein. The sensor housing may be rigid.

In aspects, a sheath is slidably disposed about the elongated flexible body and is movable between an extended position, wherein the sheath extends distally at least to a distal end of the screw member, and a retracted position, wherein the sheath is positioned proximally of the screw member to expose the screw member.

In aspects, the at least one location sensor includes a plurality of sensor components configured to enable detection of the location of the sensor assembly in six degrees of freedom, although other sensor configurations are also contemplated.

In aspects, the elongated flexible body includes an outer member and an inner member disposed within the outer member. The outer member is rotatable about and relative to the inner member and defines a distal end that extends beyond a distal end of the inner member. In such aspects, the sensor assembly is engaged to the distal end of the inner member, extends distally from the inner member, and is disposed within the outer member. Further, in such aspects, the screw member is engaged to the distal end of outer member and extends distally from the outer member such that rotation of the outer member effects rotation of the screw member relative to the inner member and the sensor assembly.

BRIEF DESCRIPTION OF THE DRAWINGS

Various aspects and features of the present disclosure are described hereinbelow with references to the drawings, wherein.

DETAILED DESCRIPTION

Devices, systems, and methods for navigating a biopsy tool to a target location and obtaining a tissue sample using the biopsy tool are provided in accordance with the present disclosure and described in detailed below. The biopsy tool of the present disclosure, for example, generally includes a flexible body, a screw disposed at the distal end of the flexible body, and a sensor assembly integrated into the biopsy tool and positioned proximally adjacent the screw. The screw defines a helical configuration having a hollow interior and is configured for simultaneous rotation relative to tissue and advancement into tissue to obtain a tissue sample. The sensor assembly enables determination of the current location of the screw, thus facilitating navigation of the screw to target tissue and/or manipulation of the screw relative to target tissue. Detailed embodiments of such devices, systems incorporating such devices, and methods using the same as described below. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in virtually any appropriately detailed structure.

Figure 1:
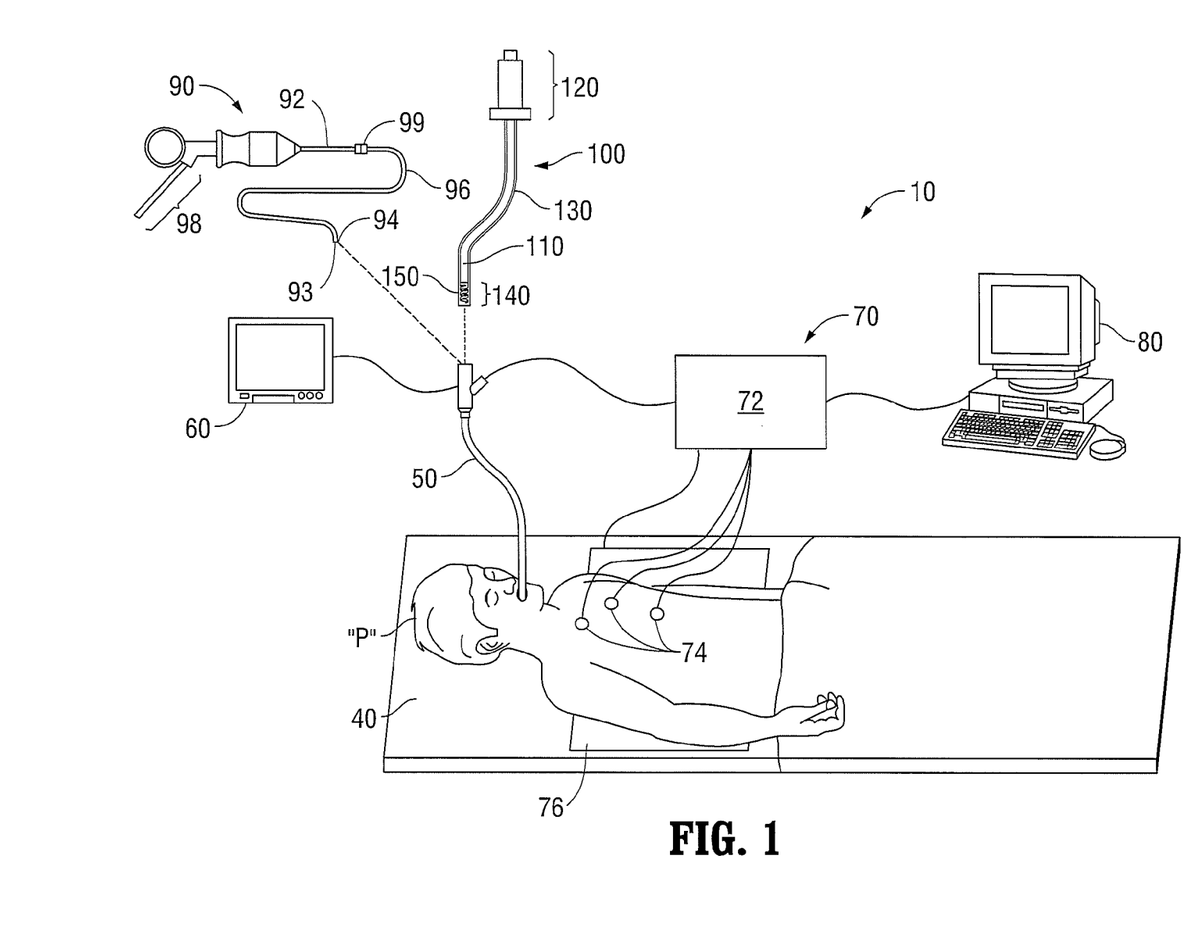
FIG. 1 is a perspective view of a system provided in accordance with the present disclosure configured for navigating a biopsy tool to a target location and obtaining a tissue sample using the biopsy tool.

With reference to FIG. 1, a system provided in accordance with the present disclosure and configured for planning a pathway to target tissue (planning phase), navigating a positioning assembly to the target tissue (navigation phase), and navigating a biopsy tool to the target tissue to obtain a tissue sample from the target tissue using the biopsy tool (biopsy phase) is shown generally identified by reference numeral 10. System 10 generally includes an operating table 40 configured to support a patient "P;" a bronchoscope 50 configured for insertion through the patient's mouth into the patient's airways; monitoring equipment 60 coupled to bronchoscope 50 for displaying video images received from bronchoscope 50; a tracking system 70 including a tracking module 72, a plurality of reference sensors 74, and a transmitter mat 76; a computer 80 including software and/or hardware used to facilitate pathway planning, identification of target tissue, and navigation to target tissue; a positioning assembly 90 including an LG 92 and an EWC 96; and a biopsy tool 100 operable to obtain a tissue sample, e.g., for subsequent diagnostic testing. The planning and navigation phases will initially be detailed below, followed by a detailed description of biopsy tools provided in accordance with the present disclosure and use of such biopsy tools in conjunction with system 10 in performing the biopsy phase.

With respect to the planning phase, computer 80 utilizes computed tomographic (CT) image data for generating and viewing a three-dimensional model of the patient's airways, enables the identification of target tissue on the three-dimensional model (automatically, semi-automatically or manually), and allows for the selection of a pathway through the patient's airways to the target tissue. More specifically, the CT scans are processed and assembled into a three-dimensional CT volume, which is then utilized to generate a three-dimensional model of the patient's airways. The three-dimensional model may be displayed on a display monitor associated with computer 80, or in any other suitable fashion. Using computer 80, various views of the three-dimensional model may be provided and/or the three-dimensional model may be manipulated to facilitate identification of target tissue on the three-dimensional model and selection of a suitable pathway through the patient's airways to access the target tissue. Once selected, the pathway is saved for use during the navigation phase(s).

Continuing with reference to FIG. 1, patient "P" is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

With respect to the navigation phase, a six degrees-of-freedom electromagnetic tracking system 70, e.g., similar to those disclosed in U.S. Pat. No. 6,188,355 and published PCT Application Nos. WO 00/10456 and WO 01/67035, the entire contents of each of which is incorporated herein by reference, or other suitable positioning measuring system, is utilized for performing registration and navigation, although other configurations are also contemplated. Tracking system 70 includes a tracking module 72, a plurality of reference sensors 74, and a transmitter mat 76. Tracking system 70 is configured for use with positioning assembly 90 and biopsy tool 100, as detailed below. Positioning assembly 90 includes a LG 92 having a steerable distal tip 93 incorporating a sensor 94, an EWC 96, and a handle 98. LG 92 and EWC 96 are configured for insertion through a working channel of bronchoscope 50 into the patient's airways (although LG 92 and EWC 96 may alternatively be used without bronchoscope 50) and are selectively lockable relative to one another via a locking mechanism 99. Steerable distal tip 93 of LG 92 may be configured for steering in any suitable fashion, e.g., using a plurality of steering wires (not shown) coupled between handle 98 and distal tip 93, to facilitate maneuvering distal tip 93 of LG 92 and EWC 96 through the patient's airways. Distal tip 93 of LG 92 may further define, at-rest, a linear, curved, or angled configuration, depending on a particular purpose. Sensor 94 is integrated with distal tip 93 of LG 92 and allows monitoring of the position and orientation of distal tip 93, in six degrees of freedom, relative to the reference coordinate system. Sensor 94 of LG 92 may be configured similar to any of the sensors detailed below with respect to biopsy tool 100 (see FIGS. 6-8).

As shown in FIG. 1, transmitter mat 76 is positioned beneath patient "P." The internal configuration of transmitter mat 76 will be detailed below with reference to FIG. 9. Transmitter mat 76 and the plurality of reference sensors 74 are interconnected with tracking module 72, which derives the location of each sensor 74 in six degrees of freedom. One or more of reference sensors 74 are attached to the chest of the patient "P." The six degrees of freedom coordinates of reference sensors 74 are sent to computer 80 (which includes the appropriate software) where they are used to calculate a patient coordinate frame of reference. Registration, as detailed below, is generally performed by identifying locations in both the three-dimensional model and the patient's airways and measuring the coordinates in both systems. Further details of such a registration technique can be found in U.S. Patent Application Pub. No. 2011/0085720, the entire contents of which is incorporated herein by reference, although other suitable registration techniques are also contemplated. An exemplary embodiment of a transmitter mat 76, and the use thereof for determining location data, is detailed below.

In use, with respect to the navigation phase, LG 92 is inserted into EWC 96 such that sensor 94 projects from the distal end of EWC 96. LG 92 and EWC 96 are then locked together via locking mechanism 99. LG 92, together with EWC 96, are then inserted through bronchoscope 50 and into the airways of the patient "P," with LG 92 and EWC 96 moving in concert with one another through bronchoscope 50 and into the airways of the patient "P." Automatic registration is performed by moving LG 92 through the airways of the patient "P." More specifically, data pertaining to locations of sensor 94 while LG 92 is moving through the airways is recorded using transmitter mat 76, reference sensors 74, and tracking module 72. A shape resulting from this location data is compared to an interior geometry of passages of the three-dimensional model generated in the planning phase, and a location correlation between the shape and the three-dimensional model based on the comparison is determined, e.g., utilizing the software on computer 80. In addition, the software identifies non-tissue space (e.g., air filled cavities) in the three-dimensional model. The software aligns, or registers, an image representing a location of sensor 94 of LG 92 with an image of the three-dimensional model based on the recorded location data and an assumption that LG 92 remains located in non-tissue space in the patient's airways. This completes the registration portion of the navigation phase.

Referring still to FIG. 1, once the planning phase has been completed, e.g., the target tissue has been identified and the pathway thereto selected, and registration has been completed, system 10 may be utilized to navigate LG 92 through the patient's airway to the target tissue. To facilitate such navigation, computer 80, monitoring equipment 60, and/or any other suitable display may be configured to display the three-dimensional model including the selected pathway from the current location of sensor 94 of LG 92 to the target tissue. Navigation of LG 92 to the target tissue using tracking system 70 is similar to that detailed below with respect to the navigation of biopsy tool 100 to the target tissue and, thus, is not detailed here for purposes of brevity.

Once LG 92 has been successfully navigated to the target tissue, completing the navigation phase, LG 92 may be unlocked from EWC 96 and removed, leaving EWC 96 in place as a guide channel for guiding biopsy tool 100 to the target tissue. Details of biopsy tool 100, along with the use of the same in the biopsy phase, are described below.

Figure 2:
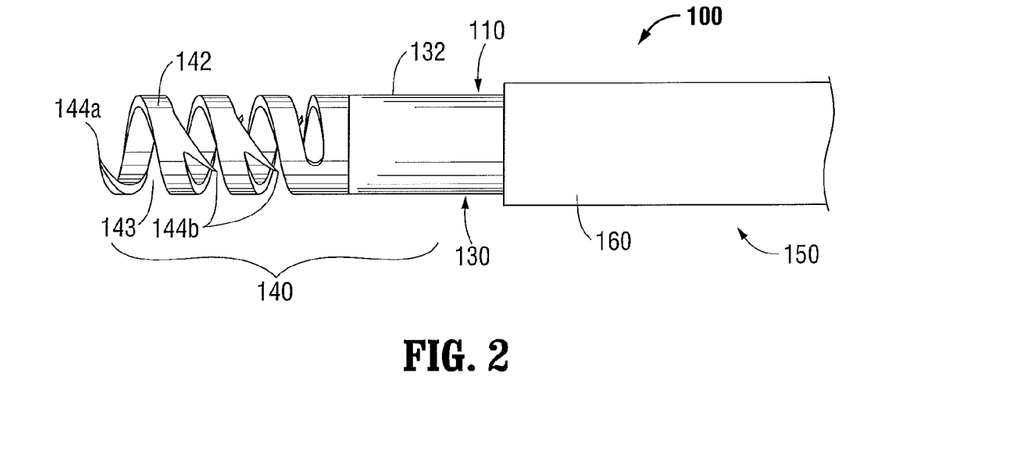
FIG. 2 is a side view of the distal end of the biopsy tool of FIG. 1 with the sheath disposed in the retracted position
Figure 3:
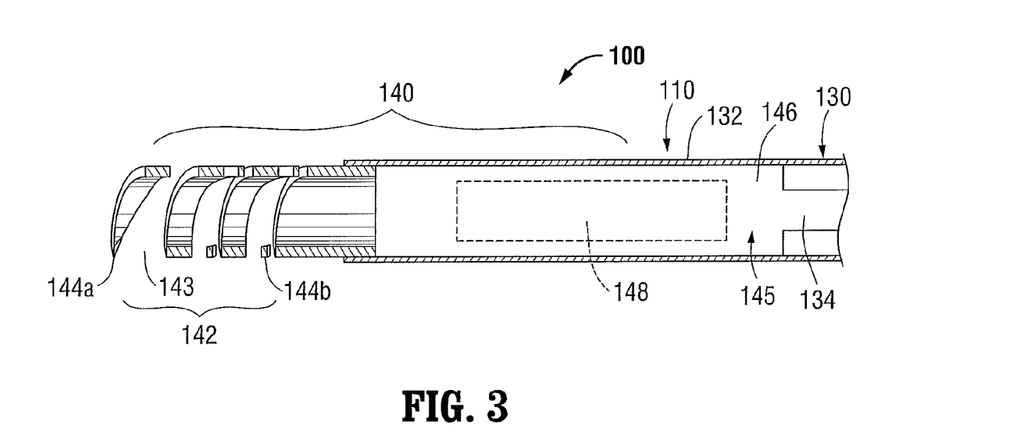
FIG. 3 is a side, cross-sectional view of the distal end of the biopsy tool of FIG. 1 with the sheath removed therefrom.
Figure 4A:
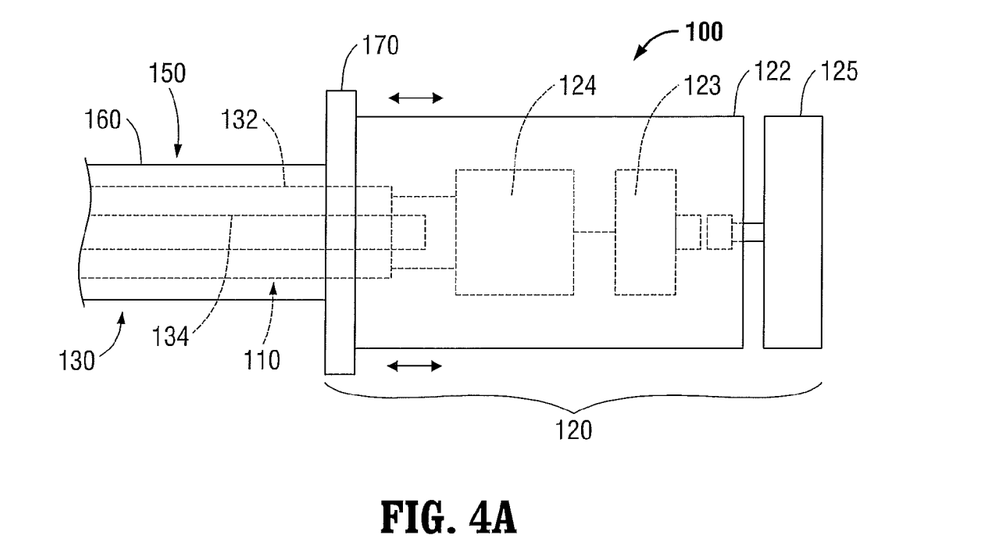
FIG. 4A is a side view of the proximal end of the biopsy tool of FIG. 1 illustrating the proximal handle portion thereof.

Referring now to FIGS. 2-4A, in conjunction with FIG. 1, as mentioned above, biopsy tool 100 is provided in accordance with the present disclosure for obtaining a tissue sample from the target tissue. As detailed below, biopsy tool 100 is further configured for use in conjunction with tracking system 70 to facilitate navigation of biopsy tool 100 to the target tissue and/or tracking of biopsy tool 100 as it is manipulated relative to the target tissue to obtain the tissue sample. Although registration and navigation are detailed above with respect to LG 92 of positioning assembly 90, it is also envisioned that LG 92 be eliminated and biopsy tool 100 itself be utilized for registration and navigation, similarly as detailed above with respect to LG 92. Biopsy tool 100 generally includes a biopsy assembly 110 and a sheath assembly 150 slidably disposed about biopsy assembly 110. However, in some embodiments, sheath assembly 150 need not be provided but, rather EWC 96 (FIG. 1) may serve the function of sheath assembly 150. Biopsy assembly 110 includes a proximal handle portion 120, an elongated flexible body portion 130, and a rigid distal end portion 140. As shown in FIG. 4, proximal handle portion 120 includes a housing 122 that encloses the inner operating components of biopsy assembly 110, e.g., battery 123 and drive motor 124. Housing 122 may further be configured to house a memory (e.g., an EEPROM) storing a variety of information regarding biopsy tool 100. For example, the memory may include identification information that can be used by the drive motor 124 to ensure that only properly identified biopsy tools 100 are connected thereto, e.g., in embodiments where proximal handle portion 120 is detachable from elongated flexible body portion 130 and/or rigid distal end portion 140. In addition, the memory may store operating parameters of the biopsy tool 100, e.g., power, time, RPM limits, and information regarding the usage of biopsy tool 100. Usage monitoring may enable limiting re-use of biopsy tool 100 beyond a certain number of activations, amount of activation time, or may limit biopsy tool 10 to a single use. Such usage limitations may optionally be reset via reprocessing as is commonly understood in the art.

An actuator 125 is operably coupled to housing 122 at the proximal end thereof and is selectively actuatable to activate drive motor 124, e.g., by completing a circuit including battery 123 and drive motor 124, to drive rotation of biopsy assembly 110, as detailed below. Alternatively, biopsy assembly 110 may be configured to connect to a remote drive and/or power source, or may be manually driven. A selection switch (not shown) operably coupled to drive motor 124 may also be provided for allowing a user to select a direction of rotation of biopsy assembly 110, e.g., to effect either clockwise or counter-clockwise rotation of biopsy assembly 110.

Body portion 130 of biopsy assembly 110 is coupled to and extends distally from proximal handle portion 120. More specifically, body portion 130 includes an outer member 132 that is coupled to drive motor 124 and rotatably engaged to housing 122, and an inner member 134 that extends through outer member 132 and is engaged to housing 122. Both of outer and inner members 132, 134 are flexible to permit insertion of body portion 130 through a patient's airways, and are rotatable relative to one another, e.g., outer member 132 is rotatable about inner member 134 relative to housing 122 upon activation of drive motor 124. As shown in FIG. 3, the distal end of outer member 132 extends distally beyond the distal end of inner member 134. Alternatively, inner member 134 need not be provided, or inner member 134 may be configured to rotate relative to housing 122 while outer member 132 is fixed relative to housing 122.

Referring to FIGS. 2 and 3, distal end portion 140 of biopsy assembly 110 is disposed at the distal end of elongated flexible body portion 130 and includes a screw member 142 and a sensor assembly 145. Screw member 142 is fixedly engaged to the distal end of outer member 132 such that rotation of outer member 132 effects similar rotation of screw member 142. Screw member 142 is rigidly formed from stainless steel or other suitable material and defines a helical configuration having a hollow interior 143 configured to receive and retain a tissue sample, as detailed below. Screw member 142 further defines a pointed distal tip 144a and a plurality of proximally-facing barbs 144b. Distal tip 144a facilitates advancement of screw member 142 through tissue and about the tissue sample, while proximally-facing barbs 144b facilitate coring of tissue about the tissue sample.

Sensor assembly 145, as shown in FIG. 3, includes a sensor housing 146 engaged to the distal end of inner member 134. Since the distal end of outer member 132 extends distally beyond the distal end of inner member 134, sensor housing 146 is disposed within outer member 132, proximally of screw member 142. In embodiments where inner member 134 is not provided, sensor assembly 145 may be engaged within outer member 132 toward the distal end thereof and proximally of screw member 142. Sensor housing 146 encloses a sensor 148 therein and is rigidly formed from any suitable material that does not interfere with the operation of sensor 148. Sensor 148, in conjunction with tracking system 70 (FIG. 1), enables tracking of distal end portion 140 of biopsy assembly 110 as distal end portion 140 is advanced through the patient's airways, as detailed below. Thus, with additional reference to FIG. 1, computer 80, monitoring equipment 60, and/or any other suitable display may be configured to display the three-dimensional model and selected pathway, both of which were generated during the planning phase, along with the current location of sensor 148 of distal end portion 140 to facilitate navigation of distal end portion 140 to the target tissue and/or manipulation of distal end portion 140 relative to the target tissue. Various sensors 148 suitable for use with biopsy assembly 110 for this purpose are detailed below (see FIGS. 6-8).

Sheath assembly 150, as best shown in FIGS. 2 and 4A, includes and elongated sheath 160 and a slider 170 engaged to sheath 160 at the proximal end of sheath 160. Sheath 160 is slidably disposed about distal end portion 140 and body portion 130 of biopsy assembly 110 and may be dimensioned to generally approximate the outer radial dimension of distal end portion 140 of biopsy assembly 110, such that biopsy tool 100 defines a low profile configuration. Sheath 160 is movable relative to biopsy assembly 110 between an extended position (FIGS. 1 and 5A), wherein sheath 160 extends to or beyond the distal end of biopsy assembly 110 to protect biopsy assembly 110 and inhibit damage with distal end portion 140 during insertion of biopsy tool 100 through bronchoscope 50, EWC 96 and/or the patient's airways to the target tissue, and a retracted position (FIGS. 2 and 5B-5D), wherein sheath 160 is retracted to expose screw member 142 of distal end portion 140 of biopsy assembly 110. As an alternative to extension and retraction, sheath assembly 150 may be configured to be fully withdrawn from about biopsy assembly 110 once biopsy assembly 110 is positioned as desired.

With reference FIG. 4A, slider 170 is slidably disposed about housing 122 of proximal handle portion 120 of biopsy assembly 110 and, as mentioned above, is engaged to the proximal end of sheath 160. Slider 170 is selectively slidable about housing 122 to move sheath 160 between the extended position and the retracted position. A locking mechanism (not shown) may also be provided for selectively locking slider 170 in the extended and/or retracted position.

Figure 4B:
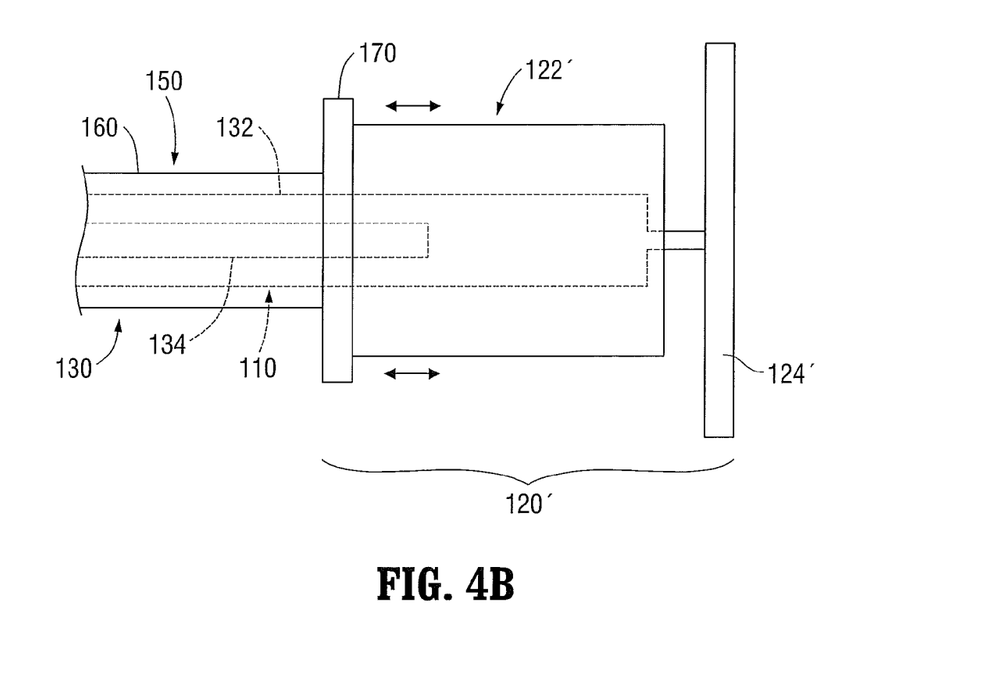
FIG. 4B is a side view of the proximal end of the biopsy tool of FIG. 1 including another embodiment of a proximal handle portion coupled thereto.

With momentary reference to FIG. 4B, as an alternative to being powered or motor-driven, biopsy assembly 110 may be additionally or alternatively configured for use with a manually-drive proximal handle portion 120'. Proximal handle portion 120' includes a housing 122' having a manually manipulatable element 124' rotatably coupled to housing 122' and operably engaged to outer member 132 for manually driving rotation of biopsy assembly 110. More specifically, upon manual rotation of element 124' relative to housing 122', outer member 132 is similarly rotated to thereby effect similar rotation of screw member 142 (FIGS. 2-3) to advance screw member 142 (FIGS. 2-3) through tissue and about a tissue sample.

Turning now to FIGS. 5A-5D, in conjunction with FIG. 1, the use of biopsy tool 100 for obtaining a tissue sample (the biopsy phase) is described. Once the planning and navigation phases have been completed, and LG 92 removed from EWC 96, biopsy tool 100, with sheath 160 disposed in the extended position, may be inserted through bronchoscope 50 and EWC 96, to the target tissue. Sensor 148 of biopsy tool 100, in conjunction with tracking system 70, as mentioned above, enable tracking of sensor 148 as it is advanced through the patient's airways. Thus, even after distal end portion 140 is extended distally from EWC 96, the position of distal end portion 140 can be tracked, thus permitting navigation of screw member 142 to and/or manipulation of screw member 142 relative to the target tissue to ensure proper positioning of screw member 142 relative to the target tissue and allowing certain tissue structures adjacent the target tissue to be avoided. Tracking and navigating using sensor 148 and tracking system 70 will be described in greater detail below, following the description of the various embodiments thereof.

Figure 5A:
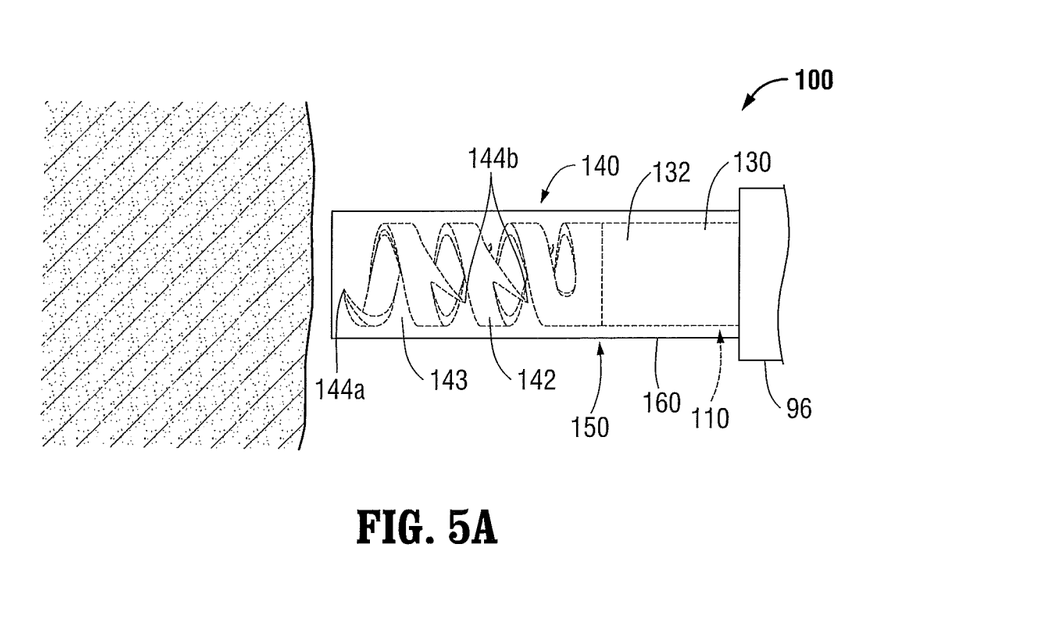
FIGS. 5A-5D progressively illustrate use of the biopsy tool of FIG. 1 for obtaining a tissue sample.
Figure 5B:
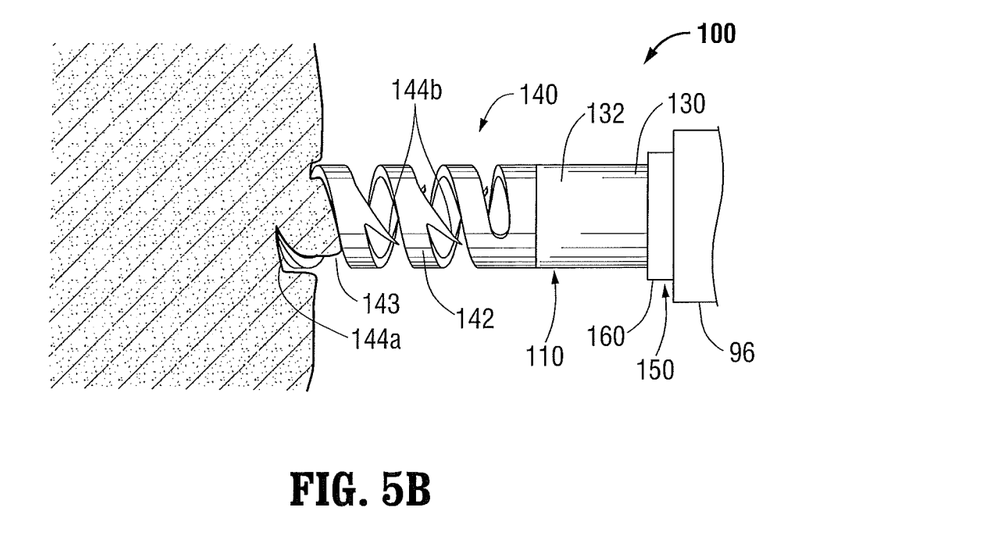
Figure 5C:
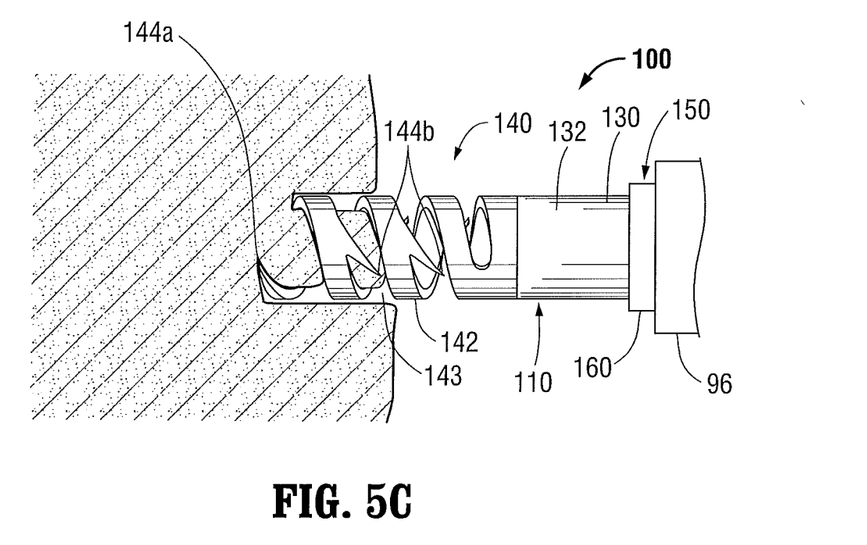
Figure 5D:
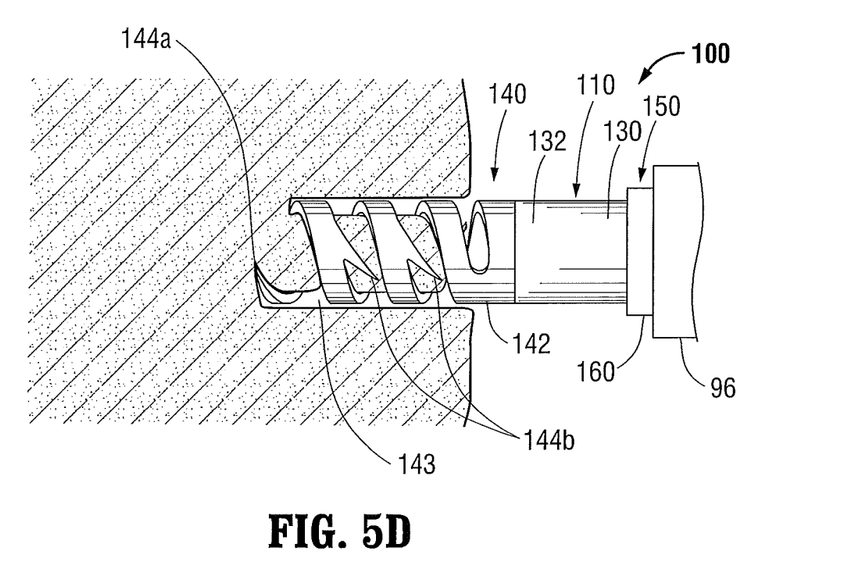

Referring to FIG. 5A, once distal end portion 140 of biopsy assembly 110 is positioned as desired, sheath 160 may be moved from the extended position to the retracted position, e.g., via sliding slider 170 proximally about housing 122 (FIG. 4A), to expose screw member 142. Turning to FIGS. 5B-5D, with screw member 142 exposed and positioned adjacent the target tissue, screw member 142 may be activated, e.g., by actuating actuator 125 to activate drive motor 124 to drive rotation of outer member 132 and, thus, screw member 142. More specifically, screw member 142 may be activated to rotate in a first direction such screw member 142 is lead by distal tip 144a during advancement into tissue. Sensor assembly 145 (FIG. 3), which is engaged to inner member 134, is not rotated in conjunction with screw member 142 but, rather, as mentioned above, screw member 142 and outer member 132 are rotated about and relative to inner member 134 and, thus sensor assembly 145. As such, the orientation and position of sensor 148 (FIG. 3) can still be readily determined and displayed to the operator, even while screw member 142 is actively rotating. Alternatively, as mentioned above, inner member 134 need not be provided and sensor assembly 145 may be engaged within outer member 132 such that sensor assembly 145 is rotated therewith.

Continuing with reference to FIGS. 5B-5D, with screw member 142 activated, e.g., rotating relative to the target tissue in the first direction, screw member 142 may be advanced into the target tissue such that a tissue sample is received within hollow interior 143 of screw member 142 while distal tip 144a and proximally-facing barbs 144b facilitate coring of tissue about the tissue sample. Sensor 148 (FIG. 3) enables the tracking of screw member 142 during tissue sampling such that the surgeon can readily ascertain the depth of screw member 142 relative to tissue, the angle of insertion, etc., thus helping to ensure a suitable tissue sample is obtained with minimal tissue damage. Although sensor 148 (FIG. 3) is displaced from screw member 142, the construction of distal end portion 140 of biopsy assembly 110 enables accurate determination of the positioning of screw member 142 within the patient's airways and relative to the target tissue. In fact, the software of computer 80 (FIG. 1) may be configured to provide for the display of screw member 142 based upon the location data of sensor 148 (FIG. 3) received from tracking system 70 (FIG. 1), as screw member 142 is disposed at a fixed distance and angle relative to sensor 148 (FIG. 3), although the rotational orientation of screw member 142 relative to sensor 148 (FIG. 3) is variable.

Once a sufficient tissue sample has been received and retained within hollow interior 143 of screw member 142, actuator 125 (FIG. 4A) may be released (or otherwise returned to an un-actuated position), to deactivate drive motor 124 (FIG. 4A) and stop rotation of outer member 132 and screw member 142. Additionally, where advantageous, drive motor 124 (FIG. 4A) may be activated to rotate in a second, opposite direction at this point to facilitate shearing or coring about the tissue sample with barbs 144b to ensure full separation of the tissue sample from the target location and retention of the tissue sample within hollow interior 143. Thereafter, biopsy tool 100 may be withdrawn from the patients airways, EWC 96, and bronchoscope 50 (FIG. 1) and the tissue sample retrieved therefrom for diagnostic testing or other purposes. Sheath 160 may be returned to the extended position prior to withdrawal, or may be left in the retracted position during withdrawal of biopsy tool 100.

Figure 6:
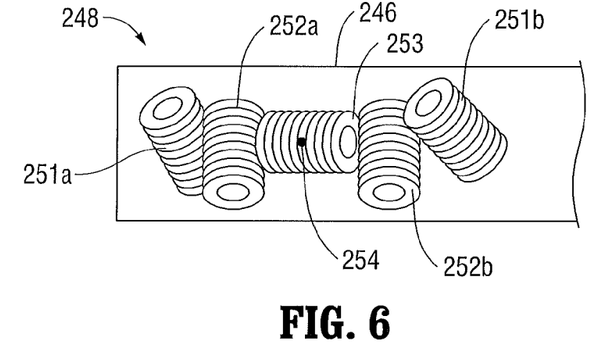
FIG. 6 is a perspective view of a sensor configured for use with the biopsy tool of FIG. 1.
Figure 7:
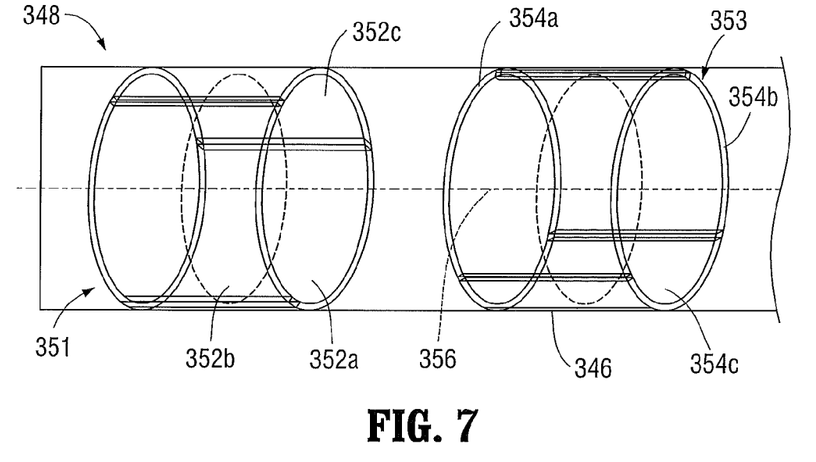
FIG. 7 is a perspective view of another sensor configured for use with the biopsy tool of FIG. 1.
Figure 8:
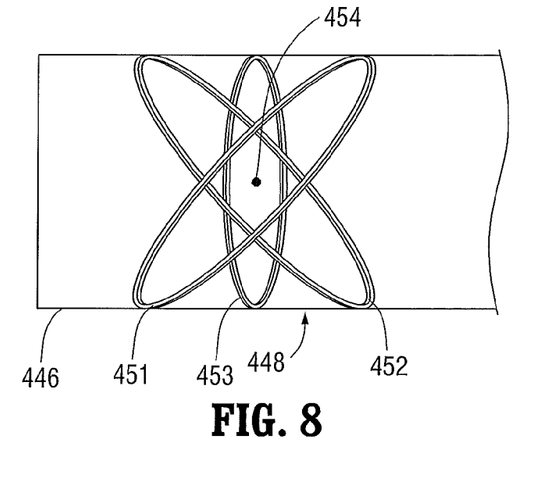
FIG. 8 is a perspective view of another sensor configured for use with the biopsy tool of FIG. 1.

Turning now to FIGS. 6-8, in conjunction with FIG. 1, various different sensors 248, 348, 448 (FIGS. 6-8, respectively) configured for use as sensor 148 of sensor assembly 145 of biopsy tool 100 (see FIG. 3), and/or sensor 94 of LG 92 are described. Referring to FIG. 6, sensor 248 is shown. Sensor 248 includes a plurality of field component sensor elements 251a, 251b, 1252a, 252b, 253. Each sensor element 251a, 251b, 252a, 252b, 253 is formed as a coil and arranged for sensing a different component of an electromagnetic field generated by transmitter mat 76 (FIG. 9). More specifically, first and second pairs of sensor elements 251a, 251b and 252a, 252b are arranged within sensor housing 246 such that the respective elements 251a, 251b and 252a, 252b of each pair are equidistant from a common reference point 254, while sensor element 253 is centered about reference point 254. Although shown in FIG. 6 as collinearly disposed, other configurations of sensor elements 251a, 251b, 1252a, 252b, 253 are also contemplated. Further, as opposed to providing five sensor elements 251a, 251b, 1252a, 252b, 253 wherein sensor element 253 is centered about the reference point 254, six sensors may be provide, e.g., wherein sensor element 253 is provided as a pair of elements disposed equidistant from reference point 254. The above-described configuration of sensor 248 enables transmitter mat 76 and the plurality of reference sensors 74 (FIG. 1), together with tracking module 72 and computer 80 (FIG. 1), to derive the location of sensor 248 in six degrees of freedom, as detailed below, and as further detailed in U.S. Pat. No. 6,188,355 and published PCT Application Nos. WO 00/10456 and WO 01/67035, previously incorporated herein by reference.

With reference to FIG. 7, sensor 348 is shown including two sensor components 351, 353 arranged within sensor housing 346, each component 351, 353 including three sensor elements 352a, 352b, 352c and 354a, 354b, 354c, respectively. Each sensor element 352a, 352b, 352c and 354a, 354b, 354c is configured as a flat rectangular coil, e.g., including a plurality of turns of conducting wire, bent to define an arcuate shape. As such, the elements 352a, 352b, 352c and 354a, 354b, 354c combine to define first and second generally cylindrical components 351, 353. Components 351, 353 are centered about reference axis 356 and positioned such that each of elements 352a, 352b, 352c and 354a, 354b, 354c are equidistant from reference axis 356 and such that each of elements 352a, 352b, 352c of component 351 are oriented 180 degrees offset as compared to corresponding elements 354a, 354b, 354c, respectively, of component 353. Thus, similarly as with sensor 248 (FIG. 6), sensor 348 enables transmitter mat 76 and the plurality of reference sensors 74 (FIG. 1), together with tracking module 72 and computer 80 (FIG. 1), to derive the location of sensor 348 in six degrees of freedom.

Turning to FIG. 8, sensor 448 includes three coils 451, 452, 453. Coils 451 and 452, 453 are angled relative to housing 446, while coil 453 is circumferentially disposed within housing 446. Coils 451, 452, 453 are oriented to lie in perpendicular planes relative to one another and share a common center reference point 454. By sharing a common center reference point 454, each portion of each coil 451, 452, 453 is equidistant from center reference point 454. Further, this configuration, e.g., wherein coils share a common center reference point 454 rather than being longitudinally displaced relative to one another, allows for the longitudinal dimension of sensor 448 to be minimized. Such a configuration still, however, enables transmitter mat 76 and the plurality of reference sensors 74 (FIG. 1), together with tracking module 72 and computer 80 (FIG. 1), to derive the location of sensor 448 in six degrees of freedom.

Figure 9:
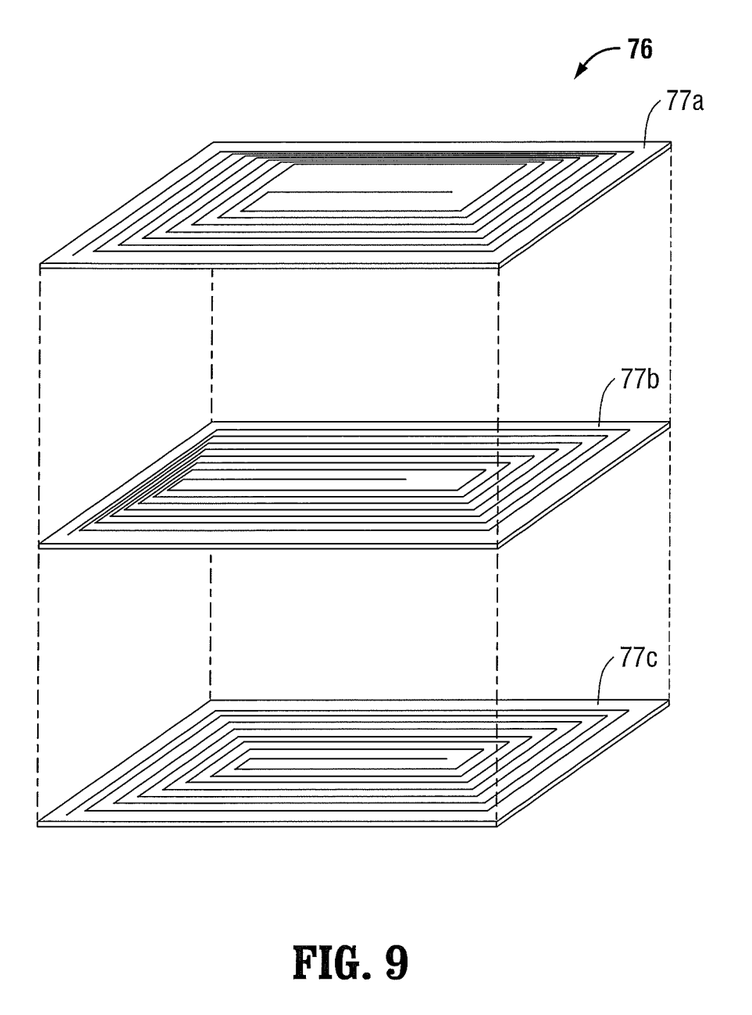
FIG. 9 is an exploded, perspective view of a transmitter mat configured for use with the system of FIG. 1 for tracking the biopsy tool through a patient's airways

Referring to FIG. 9, in conjunction with FIG. 1, an embodiment of the internal configuration of transmitter mat 76 of tracking system 70 (FIG. 1) is shown, although other suitable configurations are also contemplated. Transmitter mat 76 is a transmitter of electromagnetic radiation and includes a stack of three substantially planar rectangular loop antennas 77a, 77b, 77c configured to connected to drive circuitry (not shown).

Antenna 77a is skewed in a first horizontal direction (when the transmitter mat 76 is horizontal) in that the loops on one side of the antenna 77a are closer together than the loops on the opposite side. As a result, antenna 77a creates a magnetic field that is stronger on the side where the loops are close together than on the opposite side. By measuring the strength of the current induced by antenna 77a in the sensor assembly, e.g., sensor assembly 145 of biopsy tool 100 (FIG. 3) or sensor 94 of LG 92 (FIG. 1), it can be determined where the sensor assembly is located in the first direction over antenna 77a.

Antenna 77b is similar to antenna 77a except that antenna 77b is skewed in an second horizontal direction that is perpendicular to the first direction. By measuring the strength of the current induced by antenna 77b in the sensor assembly, it can be determined where the sensor assembly is located in the second direction over antenna 77b.

Antenna 77c defines a uniform, i.e., un-skewed, configuration. Thus, antenna 77c creates a uniform field that naturally diminishes in strength in a vertical direction when the transmitter mat 76 is horizontal. By measuring the strength of the field induced in the sensor assembly, it can be determined how far the sensor assembly is located above antenna 77c.

In order to distinguish one magnetic field from another, the fields of antennae 77a, 77b, 77c are generated using independent frequencies. For example, antenna 77a may be supplied with alternating current oscillating at 2.5 kHz, antenna 77b may be supplied with alternating current oscillating at 3.0 kHz, and antenna 77c may be supplied with alternating current oscillating at 3.5 kHz, although other configurations are also contemplated. As a result of using independent frequencies, each of the sensor components of the sensor assembly (see FIGS. 6-8, for example) will have a different alternating current signal induced in its coils.

Referring additionally to FIG. 1, in use, signal generators and amplifiers of the driving circuitry (not shown) associated with tracking system 70 are utilized to drive each of antennas 77a, 77b, 77c of transmitter mat 76 at their corresponding frequencies. The electromagnetic waves generated by transmitter mat 76 are received by the various sensor elements of the sensor assembly e.g., the sensor elements of sensors 248, 348, 448 (FIGS. 6-8, respectively) configured for use with sensor assembly 145 of biopsy tool 100 (FIG. 3) or sensor 94 of LG 92, and are converted into electrical signals that are sensed via reference sensors 74. Tracking system 70 further includes reception circuitry (not shown) that has appropriate amplifiers and A/D converters that are utilized to receive the electrical signals from reference sensors 74 and process these signals to determine and record location data of the sensor assembly. Computer 80 may be configured to receive the location data from tracking system 70 and display the current location of the sensor assembly on the three-dimensional model and relative to the selected pathway generated during the planning phase, e.g., on computer 80, monitoring equipment 60, or other suitable display. Thus, navigation of biopsy tool 100 (FIG. 3) and/or LG 92 to the target tissue and/or manipulation of biopsy tool 100 (FIG. 3) relative to the target tissue, as detailed above, can be readily achieved.

Figure 10A:
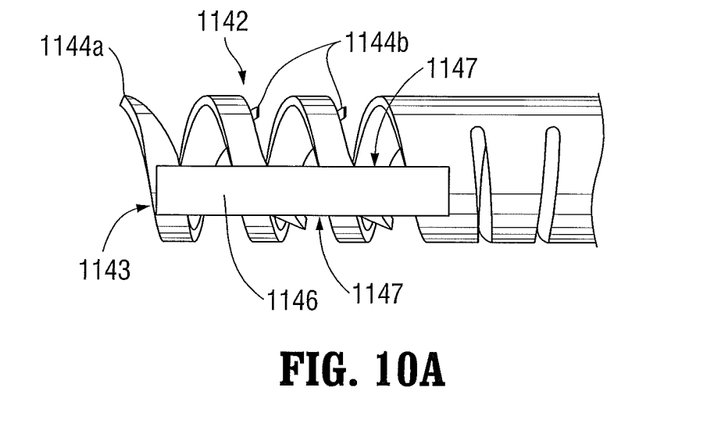
FIG. 10A is a first side view of another embodiment of a screw member configured for use with the biopsy tool of FIG. 1.
Figure 10B:
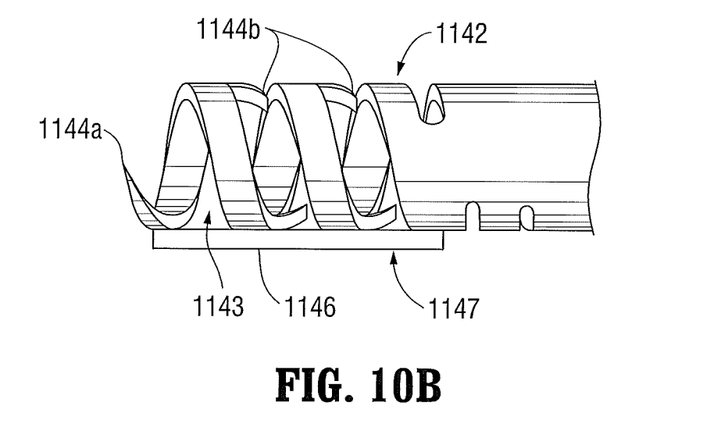
FIG. 10B is a second side view of the screw member of FIG. 10A wherein the screw member is shown rotated 90 degrees from the position of FIG. 10A.

FIGS. 10A-10B illustrates another embodiment of a screw member 1142 configured for use with biopsy assembly 110 (FIGS. 1-5D). Screw member 1142 is similar to screw member 142 (FIGS. 2-3) and, thus, only the differences therebetween will be described in detail below for purposes of brevity.

Screw member 1142 is configured for fixed engagement to the distal end of outer member 132 (FIGS. 2-3) such that rotation of outer member 132 (FIGS. 2-3) effects similar rotation of screw member 1142. Screw member 1142 defines a helical configuration having a hollow interior 1143 configured to receive and retain a tissue sample, a pointed distal tip 1144a, and a plurality of proximally-facing barbs 1144b. Screw member 1142 further includes a support plate 1146 secured to, e.g., via welding or other suitable method, the exterior surface of screw member 1142 and extending longitudinally therealong. More specifically, support plate 1146 is secured to a plurality of "turns" of the helical-shaped screw member 1142 so as to inhibit axial contraction of screw member 1142, e.g., during insertion of screw member 1142, and axial expansion of screw member 1142, e.g., during withdrawal of screw member 1142. Support plate 1146 further includes sharpened longitudinal edges 1147 configured to facilitate the coring of tissue about the tissue sample as screw member 1142 is advanced into tissue. Screw member 1142 may otherwise be configured similarly to or include any of the features of screw member 142 (FIGS. 2-3), and vice versa.

Figure 11:
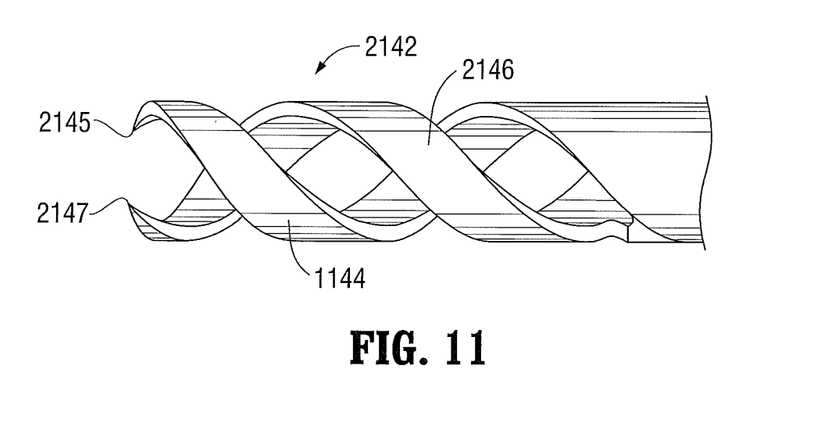
FIG. 11 is a side view of another embodiment of a screw member configured for use with the biopsy tool of FIG. 1.

Referring to FIG. 11, another embodiment of a screw member 2142 configured for use with biopsy assembly 110 (FIGS. 1-5D) is shown. Screw member 2142 is similar to screw member 142 (FIGS. 2-3) except that screw member 2142 defines a double-helix configuration having first and second screw arms 2144, 2146. Each screw arm 2144, 2146 includes a pointed distal end 2145, 2147 and may include any of the features of screw member 142 (FIGS. 2-3) and/or screw member 1142 (FIGS. 10A-10B). The double-helix configuration of screw member 2142 provides two "starts," e.g., at pointed distal ends 2145, 2147 of arms 2144, 2146, respectively, to facilitate initiation of tissue coring as screw member 2142 is initially advanced into tissue. This configuration also provide increased cutting surface area (as there are two arms as opposed to one) to facilitate coring of tissue during advancement of screw member 2142 through tissue and enables each arm to have a relatively greater pitch length while still providing a sufficient cutting effect.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A biopsy tool, comprising:
a handle:
an elongated flexible body having a proximal portion coupled to a distal portion of the handle, wherein the proximal portion is releasably coupled to the handle, the elongated flexible body defining a distal end;
a sensor assembly disposed within the elongated flexible body towards the distal end thereof and including at least one location sensor configured to enable detection of a location of the sensor assembly within a patient's airways; and
a screw member directly coupled to the distal end of the elongated flexible body and extending distally from the elongated flexible body, the screw member positioned distally of the sensor assembly, the screw member defining a helical configuration having a hollow interior and configured for simultaneous rotation relative to tissue and advancement into tissue to obtain a tissue sample within the hollow interior.

2. The biopsy tool according to claim 1, wherein the handle including a housing having a drive motor disposed within the housing, the drive motor configured to rotate the screw member.

3. The biopsy tool according to claim 2, wherein the handle further includes an actuator configured for selectively activating the drive motor.

4. The biopsy tool according to claim 3, wherein the handle further includes a battery disposed within the housing, and where actuation of the actuator completes an electrical circuit between the battery and the drive motor to activate the drive motor.

5. The biopsy tool according to claim 1, wherein the handle is configured for manual manipulation to drive rotation of the screw member.

6. The biopsy tool according to claim 1, wherein the screw member is rigid.

7. The biopsy tool according to claim 6, wherein the screw member is made of stainless steel.

8. The biopsy tool according to claim 1, wherein the screw member defines a distal cutting tip.

9. The biopsy tool according to claim 1, wherein the screw member includes at least one proximally-facing barb.

10. The biopsy tool according to claim 1, wherein the screw member includes first and second screw arms, each screw arm defining a helical configuration.

11. The biopsy tool according to claim 1, wherein the sensor assembly includes a sensor housing, the sensor housing enclosing the at least one location sensor therein.

12. The biopsy tool according to claim 11, wherein the sensor housing is rigid.

13. The biopsy tool according to claim 1, further comprising a sheath slidably disposed about the elongated flexible body and movable between an extended position, wherein the sheath extends distally at least to a distal end of the screw member, and a retracted position, wherein the sheath is positioned proximally of the screw member to expose the screw member.

14. The biopsy tool according to claim 1, wherein the at least one location sensor includes a plurality of sensor components configured to enable detection of the location of the sensor assembly in six degrees of freedom.

15. The biopsy tool according to claim 9, wherein the at least one proximally-facing barb is spaced-apart from a distal end of the screw member.

16. A biopsy tool, comprising:
an elongated flexible body defining a distal end:
a sensor assembly disposed within the elongated flexible body towards the distal end thereof and including at least one location sensor configured to enable detection of a location of the sensor assembly within a patient's airways: and
a screw member coupled to the distal end of the elongated flexible body and extending distally from the elongated flexible body, the screw member positioned distally of the sensor assembly, the screw member defining a helical configuration having a hollow interior and configured for simultaneous rotation relative to tissue and advancement into tissue to obtain a tissue sample within the hollow interior, the screw member including a support plate secured to an exterior surface of the screw member and extending longitudinally along the screw member, the support plate configured to maintain a fixed axial length of the screw member.

17. The biopsy tool according to claim 16, wherein the support plate defines sharpened longitudinal edges to facilitate cutting tissue.

18. The biopsy tool according to claim 16, wherein the support plate is affixed to at least two different turns of the screw member.

19. A biopsy tool, comprising:
an elongated flexible body defining a distal end;
a sensor assembly disposed within the elongated flexible body towards the distal end thereof and including at least one location sensor configured to enable detection of a location of the sensor assembly within a patient's airways; and
a screw member coupled to the distal end of the elongated flexible body and extending distally from the elongated flexible body, the screw member positioned distally of the sensor assembly, the screw member defining a helical configuration having a hollow interior and configured for simultaneous rotation relative to tissue and advancement into tissue to obtain a tissue sample within the hollow interior,
wherein the elongated flexible body includes an outer member and an inner member disposed within the outer member, the outer member is configured to rotate about and relative to the inner member and defining a distal end that extends beyond a distal end of the inner member,
wherein the sensor assembly is engaged to the distal end of the inner member, extends distally from the inner member, and is disposed within the outer member, and
wherein the screw member is engaged to the distal end of outer member and extends distally from the outer member such that rotation of the outer member effects rotation of the screw member relative to the inner member and the sensor assembly.

* * * * *